US008282990B2

(12) United States Patent
Kwak et al.

(10) Patent No.: US 8,282,990 B2
(45) Date of Patent: Oct. 9, 2012

(54) METHOD FOR PREPARING A BIODEGRADABLE POLYMER MICROSPHERE CONTAINING A GLUCOSE-REGULATING PEPTIDE

(75) Inventors: Hyun Hee Kwak, Seoul (KR); Ghun Il Lee, Hwaseong-si (KR); Yong Man Park, Seoul (KR); Mi Kyung Son, Yongin-si (KR); Hi Chang Yang, Yongin-si (KR); Tae Hyoung Kim, Seoul (KR); Yoon Ji Kim, Seoul (KR); Byong Moon Kim, Seoul (KR); Sung Hee Lee, Seoul (KR); Soo Hyung Kang, Yongin-si (KR); Moohi Yoo, Seoul (KR)

(73) Assignee: Dong-A Pharmaceutical, Co., Ltd., Seoul (KR)

( * ) Notice: Subject to any disclaimer, the term of this patent is extended or adjusted under 35 U.S.C. 154(b) by 0 days.

(21) Appl. No.: 12/595,434

(22) PCT Filed: Apr. 18, 2008

(86) PCT No.: PCT/KR2008/002216
§ 371 (c)(1),
(2), (4) Date: Oct. 9, 2009

(87) PCT Pub. No.: WO2008/130158
PCT Pub. Date: Oct. 30, 2008

(65) Prior Publication Data
US 2010/0129459 A1     May 27, 2010

(30) Foreign Application Priority Data
Apr. 19, 2007   (KR) .................. 10-2007-0038467

(51) Int. Cl.
*A61K 38/17*   (2006.01)
*A61K 9/14*    (2006.01)
*B05D 7/00*    (2006.01)
*B01J 13/00*   (2006.01)

(52) U.S. Cl. ............... 427/213.36; 264/4.3; 264/4.6; 424/497; 514/11.7

(58) Field of Classification Search ............... None
See application file for complete search history.

(56) References Cited

U.S. PATENT DOCUMENTS

| 4,389,330 | A  | * | 6/1983 | Tice et al. ............... 427/213.36 |
| 6,756,472 | B1 | * | 6/2004 | Hata et al. ..................... 528/354 |
| 7,205,343 | B2 | * | 4/2007 | Dellamary et al. ........... 523/218 |
| 2004/0121008 | A1 | | 6/2004 | Shiraishi et al. |

FOREIGN PATENT DOCUMENTS

| KR | 10-2003-0081179 A | 10/2003 |
| KR | 10-0805208 B1 | 2/2008 |
| WO | 88/08300 A1 | 11/1988 |
| WO | 02/49620 A2 | 6/2002 |
| WO | 2005/009356 A2 | 2/2005 |
| WO | 2005/102293 A1 | 11/2005 |
| WO | 2005/110425 A1 | 11/2005 |

OTHER PUBLICATIONS

Wei Wu, et al., "Preparation and Characterization of Fluorouracil-loaded Poly(d,l-lactide) Microspheres," China Pharmacist 2000, vol. 3, No. 6, pp. 326-327.
Fenglan Song et al., "Studies on Preparation and Physicochemical Properties of Recombined Human Interferon - α Microspheres," China Pharmacy, 2007, vol. 18, No. 10, pp. 752-754.

\* cited by examiner

*Primary Examiner* — Robert Landsman
*Assistant Examiner* — Ian Dang
(74) *Attorney, Agent, or Firm* — Lucas & Mercanti, LLP (57) ABSTRACT

Disclosed are biodegradable microspheres, capable of releasing a glucose-regulating peptide in a controlled manner, comprising a biodegradable polymer carrier with the glucose-regulating peptide encapsulated therein, and methods for the preparation thereof. In addition to ensuring high encapsulation efficiency and high stability of the encapsulated drug, the microspheres shows neither an initial burst effect nor incomplete release and allows the zero-order release of drugs over a prolonged period of time, thus improving the therapeutic effect of the drug.

16 Claims, 5 Drawing Sheets

METHOD FOR PREPARING A BIODEGRADABLE POLYMER MICROSPHERE CONTAINING A GLUCOSE-REGULATING PEPTIDE

CROSS-REFERENCE TO RELATED APPLICATIONS

This application is a 371 of PCT/KR2008/002216 filed on Apr. 18, 2008, which claims the benefit of Korean Patent Application No. 10-2007-0038467 filed on Apr. 19, 2007, the contents of each of which are incorporated herein by reference.

TECHNICAL FIELD

The present invention relates to a biodegradable polymeric microsphere comprising a biodegradable polymer carrier with a glucose-regulating peptide encapsulated therein, capable of releasing the glucose-regulating peptide in a controlled manner, and a method for the preparation thereof.

BACKGROUND ART

After being administered orally, most protein and peptide drugs lose their active structures in the acidic environment of the stomach or undergo enzymatic degradation. Also, they are adsorbed at very low rates through the gastric or intestinal mucosa. For these reasons, protein or peptide drugs usually take non-oral administration routes, that is, are usually administered by injection. The non-oral administration of protein or peptide drugs must be repeated because most non-orally administered protein or peptide drugs show short half lives and low bioavailability in the body. In addition, their administration may be continued for a long time period, e.g., months, in many cases. In order to avoid these problems, active research into sustained-release dosage formulations has been conducted, resulting in the use of biodegradable polymeric carriers with protein or peptide drugs encapsulated therein, which can release the protein or peptide drugs therefrom as the biodegradation of the polymeric carriers progresses [Heller, J. et al., Controlled release of water-soluble macromolecules from bioerodible hydrogels, Biomaterials, 4, 262-266, 1983; Langer, R., New methods of drug delivery, Science, 249, 1527-1533, 1990; Langer, R., Chem. Eng. Commun., 6, 1-48, 1980; Langer, R. S. and Peppas, N. A., Biomaterials, 2, 201-214, 1981; Heller, J., CRC Crit. Rev. Ther. Drug Carrier Syst., 1(1), 39-90, 1984; Holland, S. J. Tighe, B. J. and Gould, P. L., J. Controlled Release, 155-180, 1986].

Aliphatic polyesters, currently used as polymeric carriers for protein or peptide drugs, received FDA permission for the use thereof because their biocompatibility was recognized. They are widely used as carriers for drug delivery or sutures for operations. Concrete examples of aliphatic polyesters include poly-L-lactic acid, polyglycolic acid, poly-D-lactic acid-co-glycolic acid, poly-L-lactic acid-co-glycolic acid, poly-D,L-lactic acid-co-glycolic acid (hereinafter referred to as 'PLGA'), poly-caprolactone, poly-valerolactone, poly-hydroxy butyrate and poly-hydroxy valerate [Peppas, L. B., Int. J. Pharm., 116, 1-9, 1995].

With the development of high-molecular weight peptides or proteins as novel therapeutics in recent years, various attempts have been made to release them from polymeric carriers in a controlled manner. The dosage forms comprising polyester microspheres with protein drugs encapsulated therein, however, suffer from the disadvantages of showing an initial burst effect, an uncontrolled release rate for a period of time due to various factors, or an incomplete release of the encapsulated drug.

For example, model protein drugs, such as bovine serum albumin, lysozyme, etc. are released in large amounts in an initial stage, but show a final release of around 50% [Crotts, G. and Park, T. G., J. Control. Release, 44, 123-134, 1997; Leonard, N. B., Michael, L. H., Lee, M. M. J. Pharm. Sci., 84, 707-712]. As for microspheres using aliphatic polyester carriers with recombinant human growth hormone encapsulated therein, they initially release the drug in an amount of 30-50%, but 40-60% of the drug remains in the microspheres [Yan, C., et al., J. Control. Release, 32, 231-241, 1994; Kim, H. K. and Park, T. G., Biotechnol. Bioeng., 65, 659-667, 1999].

The initial burst release of the drug is attributed to the fact that proteinous drugs aggregated at or adsorbed to microsphere surfaces or holes are released through rapid diffusion in an initial stage.

Proteinous drugs may be denatured by the interface between water and an organic solvent during the manufacture of microspheres, and thus form irreversible aggregates which lead to unstable release. In order to prevent the interface-induced denaturation of proteinous drugs, the use of surfactants (e.g., non-ionic type surfactant Tween, Pluronic F68, Brij 35, etc.) and stabilizers (e.g., mannitol, gelatin, trehalose, carboxymethylcellulose, etc.) or an organic solvent free of water in the preparation of microspheres has been reported [Gombotz, W. R., Healy, M., Brown, L., U.S. Pat. No. 5,019, 400].

In order to solve the problem of uncontrollable drug release rates for a period of time and the incomplete release of encapsulated drugs, many recent studies are associated with alternative methods of preparing microspheres for the sustained release of drugs, which include encapsulating a drug in a mixture of two or more polymers with different degradation rates at a predetermined ratio [Ravivarapu, H. B., Burton, K., Deluca, P. P., Eur J Pharm Biopharm 50(2) 263-270, 2000; Korean Patent Application No. 1998-0062142] or mixing two or more polymeric microspheres having different degradation rates with respective drugs encapsulated therein at a predetermined ratio (U.S. Pat. No. 4,897,268), thereby controlling both the initial release and the continuous release of the drug or drugs from the microspheres. In the microspheres prepared by the conventional methods, however, the products degraded from the polymer with a high degradation rate, e.g., lactic acid and glycolic acid, decrease the pH value, which promotes the degradation of the polymer having a low degradation rate, resulting in a release rate quite different from the calculated means of the release rates of the drugs encapsulated in respective polymers. Further, the preparation of two or more microspheres for one dosage form is disadvantageous in terms of manufacturing processes and economy (Korean Patent Application No. 2000-0036178).

As techniques for preparing microspheres, phase separation (U.S. Pat. No. 4,673,595, Korean Pat. Application No. 2007-0031304), spray-drying (Korean Pat. Application No. 2003-0023130) and organic solvent evaporation (U.S. Pat. No. 4,389,330) are generally known. In a phase separation method, a methylene chloride solvent is used in combination with silicon oil, heptene and ethyl alcohol, but all of them have to be eliminated and thus are economically disadvantageous. As for the spray-drying method, it may incur the denaturation of a peptide or proteinous drug because it requires the spray-drying of the peptide or proteinous drug at a high temperature, such as 60° C. or higher, along with an organic solvent. For these reasons, the organic solvent evaporation method is most widely applied to the preparation of peptide or proteinous drugs. One of the most technically important factors in this method is encapsulation efficiency (Korean Patent Application No. 2003-0081179).

Therefore, there is the need for a preparation method of microspheres that shows neither an initial burst effect nor incomplete release, allows the zero-order release of drugs, is simple and economically advantageous and ensures high encapsulation efficiency and high stability of the encapsulated drug.

Glucose-regulating peptides belong to a group of peptides which have therapeutic potential for the treatment of insulin-dependent diabetes mellitus, gestational diabetes mellitus or insulin-independent diabetes mellitus, obesity and lipid dysmetabolism (U.S. Pat. No. 6,506,724). Examples of glucose-regulating peptides include Exendin-3, Exendin-4 and homologs and agonists thereof, and glucagons, glucagons-like peptides (e.g., GLP-1, GLP-2) and homologs and agonists thereof (Korean Patent Application No. 2006-7015029).

Exendin-4, isolated from the salivary secretions of the lizard *Heloderma horridum* or *Heloderma suspectum*, is a physiologically active peptide consisting of 39 amino acid residues. Exendin-4 functions to stimulate the secretion of insulin from pancreatic beta cells, reduce elevated glucagons secretion and induce a decrease of appetite, thereby being useful for the treatment of diabetes and obesity [Eng. J. et al. 1990; Raufman, J. P. 1992; Goeke, R. 1993; Thorens, B. 1993].

For the effective prevention and treatment of diabetes mellitus, studies on microspheres for the sustained release of exendin-4 have been conducted (Korean Patent Application No. 2006-7023921). However, conventional methods are complicated and inefficient, as exemplified by the use and removal of many organic solvents in the phase separation method, peptide degradation attributable to the use of high energy in an ultrasonic process, and the use of many excipients including stabilizers such as sugar, and release enhancers (e.g., inorganic acids and inorganic salts).

DISCLOSURE

Technical Problem

It is therefore an object of the present invention to provide microspheres that show neither an initial burst effect nor incomplete release, allow the zero-order release of drugs irrespective of a stable release period of time, are simple and economically advantageous in the preparation thereof, and ensure high encapsulation efficiency and high stability of the encapsulated drug, and a method for the preparation thereof, which employs neither many organic solvents, high-energy treatment such as ultrasonication, nor release promoters, and are simple.

Technical Solution

In order to accomplish the above object, the present invention provides biodegradable polymeric microspheres comprising a biodegradable polymer carrier with a glucose-regulating peptide encapsulated therein, capable of releasing the glucose-regulating peptide in a controlled manner.

Also, the present invention provides a method for preparing the biodegradable polymeric microspheres.

Advantageous Effects

In addition to being simple and economically advantageous in the preparation thereof and ensuring high encapsulation efficiency and high stability of the encapsulated drug, the microspheres according to the present invention show the zero-order release of drugs, e.g., exendin-4 and thus allow the drugs to be steadily released in vitro and in vivo therefrom over three to four weeks, with neither initial burst effect nor incomplete release.

BEST MODE

Below, a detailed description is given of the present invention.

The present invention pertains to a biodegradable polymeric microsphere for the controlled release of a glucose-regulating peptide, comprising a biodegradable polymer carrier with the glucose-regulating peptide encapsulated therein.

Examples of the glucose-regulating peptide suitable for use in the present invention include natural, recombinant or synthetic exendin-3, exendin-4 and homologs and agonists thereof, glucagon, glucagon-like peptides (e.g., GLP-1, GLP-2) and homologs and agonists thereof, with preference for synthetic exendin-3, exendin-4 and homologs and agonists thereof. Most preferable is synthetic exendin-4.

The content of the glucose-regulating peptide in the microsphere may vary depending on administration routes, dosages, and protein properties.

Suitable for use as the biodegradable polymer carrier are biodegradable polyester polymers. While serving as a scaffold for the microsphere and containing a glucose-regulating peptide therein, biodegradable polyester polymers gradually degrade to thus release the glucose-regulating peptide. Examples of the biodegradable polyester polymer include poly-L-lactic acid, poly-glycolic acid, poly-D-lactic acid-co-glycolic acid, poly-L-lactic acid-co-glycolic acid, poly-D,L-lactic acid-co-glycolic acid, poly-caprolactone, poly-valerolactone, poly-hydroxy butyrate and poly-hydroxy valerate, but are not limited thereto. As long as a biodegradable polyester polymer, is usually used in the art, no particular limitations are imposed on the use thereof in the present invention. The polymer is preferably selected from a group consisting of poly-L-lactic acid, poly-D-lactic acid-co-glycolic acid, poly-L-lactic acid-co-glycolic acid, poly-D,L-lactic acid-co-glycolic acid (PLGA), and a combination thereof. More preferable is poly-D,L-lactic acid-co-glycolic acid (PLGA), alone or in combination with poly-L-lactic acid.

Also, the present invention pertains to a method for preparing the biodegradable polymeric microsphere for the controlled release of a glucose-regulating peptide.

The method for the preparation of the biodegradable polymeric microsphere comprises:

adding an organic solvent to a polymer to give a polymer solution (step 1):
dispersing a glucose-regulating peptide in the polymer solution of step 1 to give a dispersion, followed by adding an alcohol or a mixture of an alcohol and an organic acid to the dispersion to give a drug-dispersed solution (step 2); and
forming microspheres from the drug-dispersed solution of step 2 (step 3).

A detailed description will be given of the method in a stepwise manner.

First, step 1 is to yield a polymer solution.

In step 1, a polymer is dissolved in an organic solvent. The polymer is biodegradable and can be used as a carrier. Preferable is a biodegradable polyester polymer. As long as the biodegradable polymer carrier has high solubility therein and it can be easily removed through evaporation, any volatile organic solvent may be used without particular limitation. In the present invention, the organic solvent acts not only as a solubilizer for dissolving the polymer, but also as a dispersant for uniformly dispersing the glucose-regulating peptide in the polymer solution.

Examples of the organic solvent suitable for use in the present invention include methylene chloride, ethyl acetate, chloroform, acetone, dimethylsulfoxide, dimethylformamide, N-methylpyrrolidone, dioxane, tetrahydrofuran, ethylacetate, methylethylketone, acetonitrile, and combinations thereof, with preference for methylene chloride, ethylacetate and chloroform and the greatest preference for methylene chloride.

Next, step 2 is to yield a drug-dispersed solution.

In step 2, a glucose-regulating peptide is dispersed in the polymer solution. The glucose-regulating peptide is as described above. Preferably, synthetic exendin-4 is added to obtain a drug dispersion. In the drug dispersion, the ratio of the glucose-regulating peptide to the polymer (w/w) is selected within a range sufficient to dissolve the glucose-regulating peptide.

Then, alcohol alone or in combination with an organic acid is dissolved in the drug dispersion. The alcohol and the organic acid act as solubilizers capable of dissolving both the polymer and the glucose-regulating peptide. A stabilizer or a surfactant may be further added.

In the method according to the present invention, it is very important to conduct the preparation of the drug dispersion in the order of adding an organic solvent to a polymer, adding a glucose-regulating peptide, and adding alcohol or a mixture of alcohol and organic acid. When the addition order is changed, that is, when the polymer is added with the organic solvent and alcohol or a mixture of alcohol and organic acid, followed by dissolving the glucose-regulating peptide, or when a solution of the glucose-regulating peptide in alcohol or a mixture of alcohol and organic acid is added to the polymer solution, the resulting microsphere shows an incomplete release pattern.

Useful in the present invention are methyl alcohol, ethyl alcohol, isopropyl alcohol and butyl alcohol, with methyl alcohol being preferred due to high solubility for the biodegradable polymeric carrier and the glucose-regulating peptide. The alcohol which is to dissolve the drug dispersion is preferably used in as small an amount as possible, but must be sufficient to dissolve the drug dispersion. The amount may be determined depending on the kind of alcohol. In the case of methyl alcohol, the ratio of the drug dispersion to alcohol (v/v) preferably ranges from 1:1 to 6:1, and more preferably from 3:1 to 4:1 in order to completely dissolve the drug dispersion.

Also, as long as it can dissolve the polymeric carrier and the glucose-regulating peptide, any organic acid may be used without particular limitation. Examples of the organic solvent suitable for the present invention include oxalic acid, oxaloacetic acid, fumaric acid, malic acid, succinic acid, acetic acid, butyric acid, palmitic acid, tartaric acid, ascorbic acid, uric acid, sulfonic acid, sulfinic acid, formic acid, citric acid, isocitric acid, alpha-ketoglutaric acid, succinic acid and nucleic acids, with preference for acetic acid, formic acid and a combination thereof. Like the alcohol, the amount of the organic acid is determined depending on the kind thereof.

No particular limitations are imposed on additives as long as they can dissolve the drug dispersion and are soluble in a solvent for the drug dispersion. For example, polyethylene glycols (Solutol HS-15™, TPGS™, Gelucire™), oils (Labrafil™, Labrasol™, Medium Chain Triglyceride™), proteins (Lectin), surfactants (N-Methyl pyrrolidone, Polyvinyl pyrrolidone, Tween™, Span™, Cremophor™, Poloxamer™, Brij™, Sunsoft 818H™) and hydropropyl methylcellulose may be used. The concentration thereof in the solubilizer ranges from 0.01 to 15% (w/v) and preferably from 0.1 to 12.5% (w/v).

Finally, step 3 is to form microspheres from the drug-dispersed solution of step 2.

The formation of the microsphere may be achieved by dispersing the drug-dispersed solution in an aqueous solution containing an emulsifier or using a spray drier.

When the drug-dispersed solution is dispersed in an aqueous solution containing an emulsifier, a stirrer and a homogenizer are used to form microspheres, which are then dried. The emulsifier useful in the present invention may be a lipophilic emulsifier dispersible in organic solvents or a hydrophilic emulsifier dispersible in aqueous solvents. Examples of the hydrophilic emulsifier include Tween, Triton, Brij, polyvinylpyrrolidone, and polyvinylalcohol, with preference fox polyvinylalcohol. The organic solvent may or may not be saturated with the emulsifier. Methylene chloride, ethyl acetate or chloroform may be preferably used as the organic solvent, with the greatest preference for methylene chloride. The concentration of the emulsifier in aqueous solution ranges from 0.01 to 5.0% (w/v) and preferably from 0.5 to 2% (w/v).

In this step, the drying may be implemented as freeze-drying or vacuum-drying. The resulting microspheres may be harvested through centrifugation upon freeze-drying or through a vacuum filter system upon vacuum-drying before final drying.

The microspheres prepared according to the method are of an O/W type and range in mean size from 5 to 70 µm, and preferably from 10 to 30 µm, which is suitable for injection. The particle size can be set at various values by controlling the volume ratio of the oil phase, that is, the drug-dispersed solution, to the water phase in which the emulsifier is dissolved.

In the case of spray-drying, microspheres can be prepared simply by spraying the drug-dispersed solution from a spray-drier. In the interests of preparation efficiency, the spray-drier is set at 115~125° C. for the influx and at 80~90° C. for the efflux. Thereafter, the spray-dried microspheres may be allowed to undergo an additional drying process, such as freeze-drying or vacuum-drying, to remove residual solvents therefrom.

Further, the biodegradable polymeric microsphere according to the present invention may be prepared by a method comprising:
adding an organic solvent to a polymer to give a polymer solution (step 1):

emulsifying the polymer solution of step 1 with an aqueous glucose-regulating peptide solution containing a surfactant to give a primary emulsion (step 2'); and forming microspheres from the primary emulsion of step 2' (step 3').

In step 1, a polymer is dissolved in an organic solvent. The polymer is biodegradable and can be used as a carrier. Preferable is a biodegradable polyester polymer. As long as it has high solubility for the biodegradable polymer carrier and can be easily removed through evaporation, any volatile organic solvent may be used without particular limitation. In the present invention, the organic solvent acts not only as a solubilizer for dissolving the polymer, but also as a dispersant for uniformly dispersing the glucose-regulating peptide in the polymer solution.

Examples of the organic solvent suitable for use in the present invention include methylene chloride, ethyl acetate, chloroform, acetone, dimethylsulfoxide, dimethylformamide, N-methylpyrrolidone, dioxane, ethylacetate, methylethylketone, acetonitrile, and combinations thereof, with preference for methylene chloride, ethylacetate and chloroform and most preference for methylene chloride.

In step 2', an aqueous glucose-regulating peptide solution containing a surfactant is added to the polymer solution, followed by emulsification with a stirrer or a homogenizer to give a primary emulsion. Synthetic exendin-4 may be preferably employed as a glucose-regulating peptide. The addition of the aqueous glucose-regulating peptide solution containing a surfactant to the polymer solution results in the formation of W/O/W type double emulsion microspheres.

In step 2', any surfactant may be contained in the aqueous glucose-regulating peptide solution as long as it can dissolve the glucose-regulating peptide in the aqueous solution. Examples of the surfactant available in the present invention include Tween, Triton, Brij, polyvinylpyrrolidone, and polyvinylalcohol.

The formation of microspheres may be achieved by dispersing the primary emulsion of step 2' in an aqueous solution containing an emulsifier, stirring with a stirrer and a homogenizer, and drying. The emulsifier useful in the present invention may be a lipophilic emulsifier dispersible in organic solvents or a hydrophilic emulsifier dispersible in aqueous solvents. Examples of the hydrophilic emulsifier include Tween, Triton, Brij, polyvinylpyrrolidone, and polyvinylalcohol, with preference for polyvinylalcohol. An emulsifier, whether saturated in the organic solvent or not, may be used. Methylene chloride, ethyl acetate or chloroform may be preferably used as the organic solvent, with greatest preference for methylene chloride. The concentration of the emulsifier in aqueous solution ranges from 0.01 to 5.0% (w/v), and preferably from 0.5 to 2% (w/v).

In this step, the drying may resort to freeze-drying or vacuum-drying. The resulting microspheres may be harvested through centrifugation upon freeze-drying or through a vacuum filter system upon vacuum-drying before final drying.

Enjoying the advantages of showing neither initial burst effect nor incomplete release, maintaining the zero-order release of exendin-4, ensuring high encapsulation efficiency due to the simple preparation method thereof and high stability for the encapsulated exendin-4, and steadily releasing exendin-4 therefrom in vitro and in vivo over three or more weeks, the microspheres prepared according to the present invention are useful as an agent for releasing exendin-4 in a controlled manner.

MODE FOR INVENTION

A better understanding of the present invention may be obtained through the following examples which are set forth to illustrate, but are not to be construed as the limit of the present invention.

Example 1

Preparation of Microspheres According to Kinds of Polymers and Mixture Ratios (O/W Emulsion)

300 mg of a polymer (Boehringer Ingelheim) was completely dissolved in methylene chloride. In this polymer solution, 9 mg of exendin-4 (American Peptide) was dispersed to give an exendin-4 dispersion. The polymer that was used, as listed in Table 1, was one polymer product or a mixture of two different polymer products in various mixture ratios. To each of the drug dispersions which were different in polymer kind and mixture ratio, methyl alcohol was added in a predetermined amount (alcohol:drug dispersion 1:4 v/v) to give drug-dispersed solutions. 10 ml of each of the drug-dispersed solutions was emulsified with 250 ml of a methylene chloride-saturated polyvinylalcohol 1% aqueous solution (w/v) using a stirrer or a homogenizer to form microspheres. While the methylene chloride was allowed to slowly evaporate in air by stirring at room temperature for several hours under atmospheric pressure, the microspheres were solidified. Following centrifugation, the microspheres thus harvested were washed with distilled water, frozen at −70° C. and freeze-dried at room temperature under 50 mTorr for 3 days using an adVantage freeze dryer (VirTis, NY, U.S.A) to afford O/W type microspheres, which can release exendin-4 in a controlled manner.

TABLE 1

| Examples | Exendin-4 (mg) | Polymer (mg) | Kind of Polymer | Mixing Ratio |
|---|---|---|---|---|
| 1-1 | 9 | 300 | RG502H | 1 |
| 1-2 | | | RG502H:R202 | 90:10 |
| 1-3 | | | RG502H:R202 | 80:20 |
| 1-4 | | | RG502H:RG502 | 90:10 |
| 1-5 | | | RG502H:RG502 | 80:20 |
| 1-6 | | | RG502H:RG503 | 90:10 |
| 1-7 | | | RG502H:RG503 | 80:20 |

Example 2

Preparation of Microspheres According to Ratios of Alcohol to Drug Dispersion (O/W Emulsion)

300 mg of a polymer (RG502B, Boehringer Ingelheim) was completely dissolved in methylene chloride. In this polymer solution, 9 mg of exendin-4 (American Peptide) was dispersed to give an exendin-4 dispersion. To the drug dispersion were added predetermined amounts of methyl alcohol (alcohol:drug dispersion: 1:1-1:7 v/v), as shown in Table 2, to give drug-dispersed solutions. They were emulsified and dried in the same manner as in Example 1 to afford microspheres.

TABLE 2

| Examples | MeOH (Vol) | Exendin-4 Dispersion (Vol) | States of Drug-Dispersed Solution |
|---|---|---|---|
| 2-1 | 1 | 1 | Solution |
| 2-2 |   | 2 | Solution |
| 2-3 |   | 3 | Solution |
| 1-1 |   | 4 | Solution |
| 2-4 |   | 5 | Solution |
| 2-5 |   | 6 | Solution |
| 2-6 |   | 7 | Dispersion |

As shown in Table 2, a solution was not formed when the volume ratio of the drug dispersion to methyl alcohol was 7 or greater.

Example 3

Preparation of Microspheres from Drug-Dispersed Solution Containing Additive (O/W Emulsion)

Microspheres were prepared in the same manner as in Example 1-1, with the exception that various additives were mixed in an amount of 0.1 or 12.5 vol % of the solvent with the drug-dispersed solution. In Table 3, the additives and their vol % mixed with the solution are summarized.

TABLE 3

| Examples | Exendin-4 (mg) | Polymer (mg) | Additives | Mixing 0.1% | Mixing 12.5% |
|---|---|---|---|---|---|
| 3-1 | 9 | 300 | Solutol HS-15 | ○ | ○ |
| 3-2 |   |   | TPGS | ○ | ○ |
| 3-3 |   |   | Gelucire | ○ | ○ |
| 3-4 |   |   | Labrafil | ○ | ○ |
| 3-5 |   |   | Labrasol | ○ | ○ |
| 3-6 |   |   | Medium Chain Triglyceride | ○ | ○ |
| 3-7 |   |   | Lecithin | ○ | ○ |
| 3-8 |   |   | N-Methyl pyrrolidone | ○ | ○ |
| 3-9 |   |   | Polyvinyl pyrrolidone | ○ | ○ |
| 3-10 |   |   | Hydropropyl methylcellulose | ○ | ○ |
| 3-11 |   |   | Tween | ○ | ○ |
| 3-12 |   |   | Span | ○ | ○ |
| 3-13 |   |   | Cremophor | ○ | ○ |
| 3-14 |   |   | Poloxamer | ○ | ○ |
| 3-15 |   |   | Brij | ○ | ○ |
| 3-16 |   |   | Sunsoft 818H | ○ | ○ |

Figure 3:
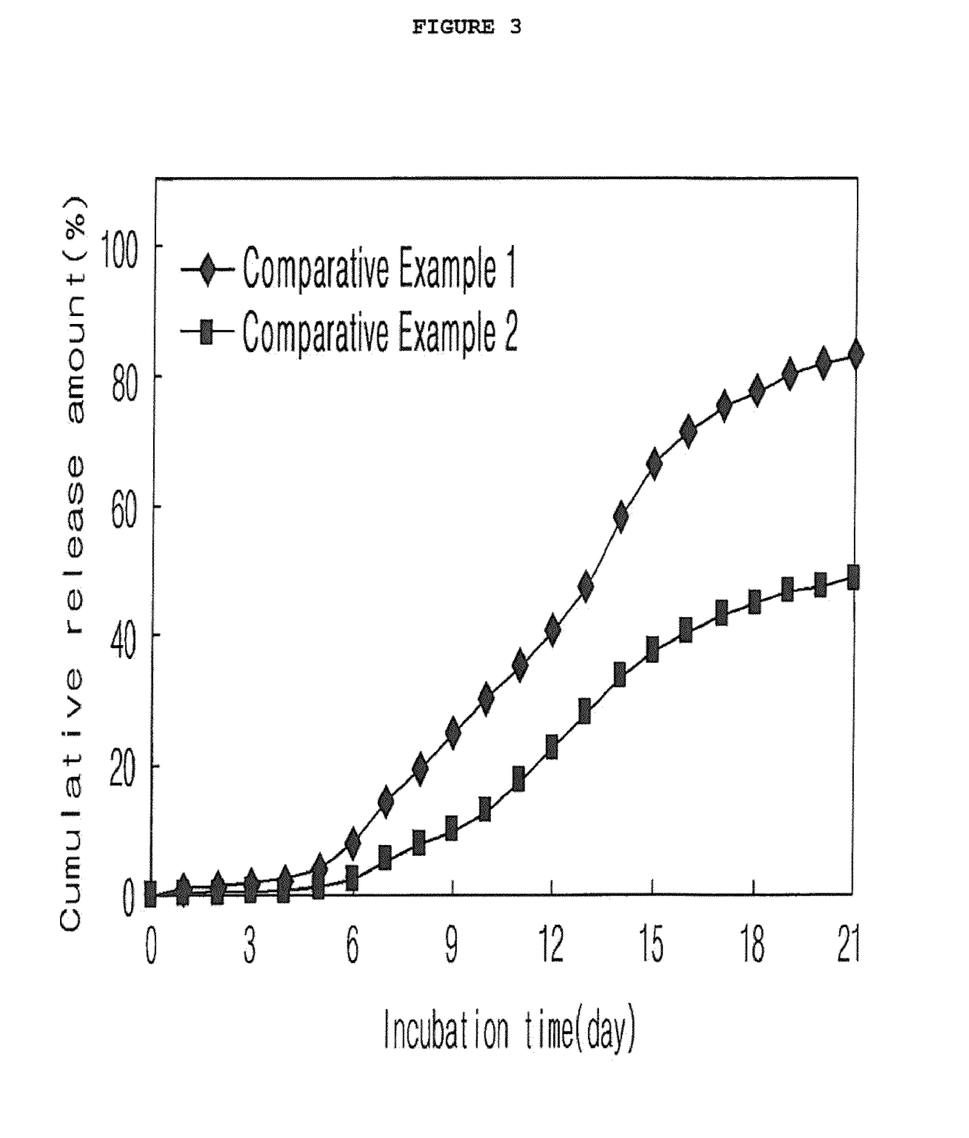
FIG. 3 is a graph showing the in vitro release patterns of the microspheres prepared in Comparative Examples 1 and 2.

As shown in FIG. 3, various additives in a broad concentration range can be mixed with the drug-dispersed solution.

Example 4

Preparation of Microspheres from Aqueous Emulsifier Solution not Saturated with Organic Solvent (O/W Emulsion)

Microspheres were prepared in the same manner as in Example 1-1 with the exception that the drug-dispersed solution was added to 250 ml of an aqueous polyvinyl alcohol 1% solution (w/v) not saturated with methylene chloride and emulsified using a stirrer or a homogenizer.

Example 5

Preparation of Microspheres Having Different Particle Sizes (O/W Emulsion)

Microspheres were prepared in the same manner as in Example 1-1 with the exception that the volume ratio of the methylene chloride-saturated polyvinyl alcohol 1% aqueous solution (w/v) to the drug-dispersed solution, that is, the volume ratio of the water phase to the oil phase, was set as shown in Table 4, below.

TABLE 4

| Examples | Exendin-4 (mg) | Polymer (mg) | Water Phase:Oil Phase (v/v) |
|---|---|---|---|
| 5-1 | 9 | 300 | 1:15 |
| 5-2 |   |   | 1:30 |
| 5-3 |   |   | 1:60 |

Example 6

Preparation of Microspheres According to Drying (O/W Emulsion)

The microspheres, solidified after the methylene chloride was gradually evaporated by stirring at room temperature under atmospheric pressure for several hours as in Example 1-1, were filtered through a vacuum filter system, washed with distilled water and dewatered before final drying at room temperature under pressure of 50 mTorr for 3 days using an advantage dryer (VirTis, NY, U.S.A).

Example 7

Preparation of Microspheres Using Spray Drying (O/W Emulsion)

The drug-dispersed solution obtained in Example 1-1 was not mixed with an aqueous emulsifier solution, but was injected at a rate of 2.5 ml per min into a spray dryer (Buchi Mini spray dryer, B-290) while being sprayed at a rate of 400 Nl/h through a 0.7 mm nozzle. The microspheres thus formed were dried in a vacuum to afford a microsphere dosage form which could steadily release exendin-4. The temperature of the spray drier was set at 120±2° C. for influx and 85±2° C. for efflux.

Example 8

Preparation of Microspheres Using Aqueous Drug Solution (W/O/W Emulsion)

300 mg of a polymer (RG502H, Boehringer Ingelheim) was completely dissolved in methylene chloride. To this polymer solution, an aqueous exendin-4 solution, obtained by dissolving 9 mg of exendin-4 (American Peptide) in 0.3 ml of a polyvinylalcohol 0.5% aqueous solution (w/v), was added, followed by stirring with a homogenizer to give a primary emulsion. 10 ml of the primary emulsion was emulsified with 250 ml of a methylene chloride-saturated, aqueous polyvinylalcohol 1% solution (w/v) using a stirrer or a homogenizer to form microspheres. While the methylene chloride was allowed to slowly evaporate in air by stirring at room temperature for several hours under atmospheric pressure, the microspheres were solidified. Following centrifugation, the microspheres thus harvested were washed with distilled water, frozen at −70° C. and freeze-dried at room temperature under 50 mTorr for 3 days using an adVantage freeze dryer (VirTis, NY, U.S.A) to afford W/O/W type microspheres which can release exendin-4 in a controlled manner.

Comparative Example 1

Preparation of O/W Type Microsphere without Drug Dispersion Process (1)

To a solution of 300 mg of a polymer (RG502H Boehringer Ingelheim) in methylene chloride, methyl alcohol was added in an amount corresponding to one fourth of the volume of methylene chloride to give a polymer/methylene chloride/methyl alcohol solution. Exendin-4 was mixed at a ratio of 9:300 exendin-4: polymer (w/w) with the polymer/methylene chloride/methyl alcohol to give a drug-dispersed solution without conducting a drug dispersion process. Microspheres were prepared from the drug-dispersed solution in the same manner as in Example 1.

Comparative Example 2

Preparation of O/W Type Microsphere without Drug Dispersion Process (2)

Microspheres were prepared in the same manner as in Example 1 with the exception that a solution of 9 mg of exendin-4 in 0.2 ml of methyl alcohol was added to a solution of 300 mg of a polymer (RG502H Boehringer Ingelheim) in 0.8 ml of methylene chloride to give a drug-dispersed solution without conducting the drug dispersion process.

Experimental Example 1

Encapsulation Efficiency of Exendin-4 within Microspheres 30 mg of each of the microspheres with exendin-4 encapsulated therein, prepared in Examples 1 and 4-8, was sufficiently dissolved in 0.5 ml of DMSO in a polystyrene vessel and added with 1.5 ml of distilled water, followed by stirring for 12 hours or longer to extract exendin-4 as an water phase. The extracted exendin-4 was quantitatively analyzed to calculate the encapsulation efficiency, which is expressed as a percentage of the actual encapsulation amount to a theoretical encapsulation amount.

Calculations are summarized in Table 5, below.

TABLE 5

| Examples | Encapsulation Efficiencies (%) |
|---|---|
| 1-1 | 85 |
| 1-2 | 86 |
| 1-3 | 88 |
| 1-4 | 81 |
| 1-5 | 83 |
| 1-6 | 84 |
| 1-7 | 80 |
| 4 | 84 |
| 5-1 | 85 |
| 5-2 | 85 |
| 5-3 | 84 |
| 6 | 85 |
| 7 | 93 |
| 8 | 83 |

As shown in Table 5, the encapsulation efficiencies of the microspheres prepared according to the present invention were calculated to be 80% or higher.

Experimental Example 2

Measurement of Mean Particle Size of Microspheres 30 mg of the microspheres with exendin-4 encapsulated therein, prepared in Examples 1 and 4-8, was dispersed in 1 L of distilled water containing Tween 20 in an amount of 0.02% (v/v), followed by measuring mean particle sizes using a particle size analyzer. The measurements are shown in Table 6, below.

TABLE 6

| Examples | Mean Particle Sizes (μm) |
|---|---|
| 1-1 | 22 |
| 1-2 | 16 |
| 1-3 | 18 |
| 1-4 | 16 |
| 1-5 | 19 |
| 1-6 | 22 |
| 1-7 | 21 |
| 4 | 26 |
| 5-1 | 8 |
| 5-2 | 25 |
| 5-3 | 65 |
| 6 | 21 |
| 7 | 59 |
| 8 | 16 |

As shown in Table 6, the microspheres prepared according to the present invention ranged, in mean particle size, from 8 to 65 μm, which is small enough to be used with small size injection needles.

Experimental Example 3

In Vitro Release of Drug from Microspheres

In the following conditions, the microspheres prepared in Examples and Comparative Examples were evaluated for exendin-4 release in vitro.

30 mg of the microspheres placed in a polystyrene vessel was dispersed in 1.5 ml of PBS (phosphate buffered saline, pH 7.4) containing Tween 20 in an amount of 0.02% (v/v). During incubation at 37° C., the dispersion was centrifuged according to the incubation time to precipitate the microspheres. The supernatant was analyzed for exendin-4 level to determine the amount of exendin-4 released from the microspheres. The precipitated microspheres were again dispersed in fresh PBS for subsequent analysis experiments. The release (%) of the exendin-4 from the microspheres is plotted against incubation time period in FIGS. 1 to 3.

Figure 1:
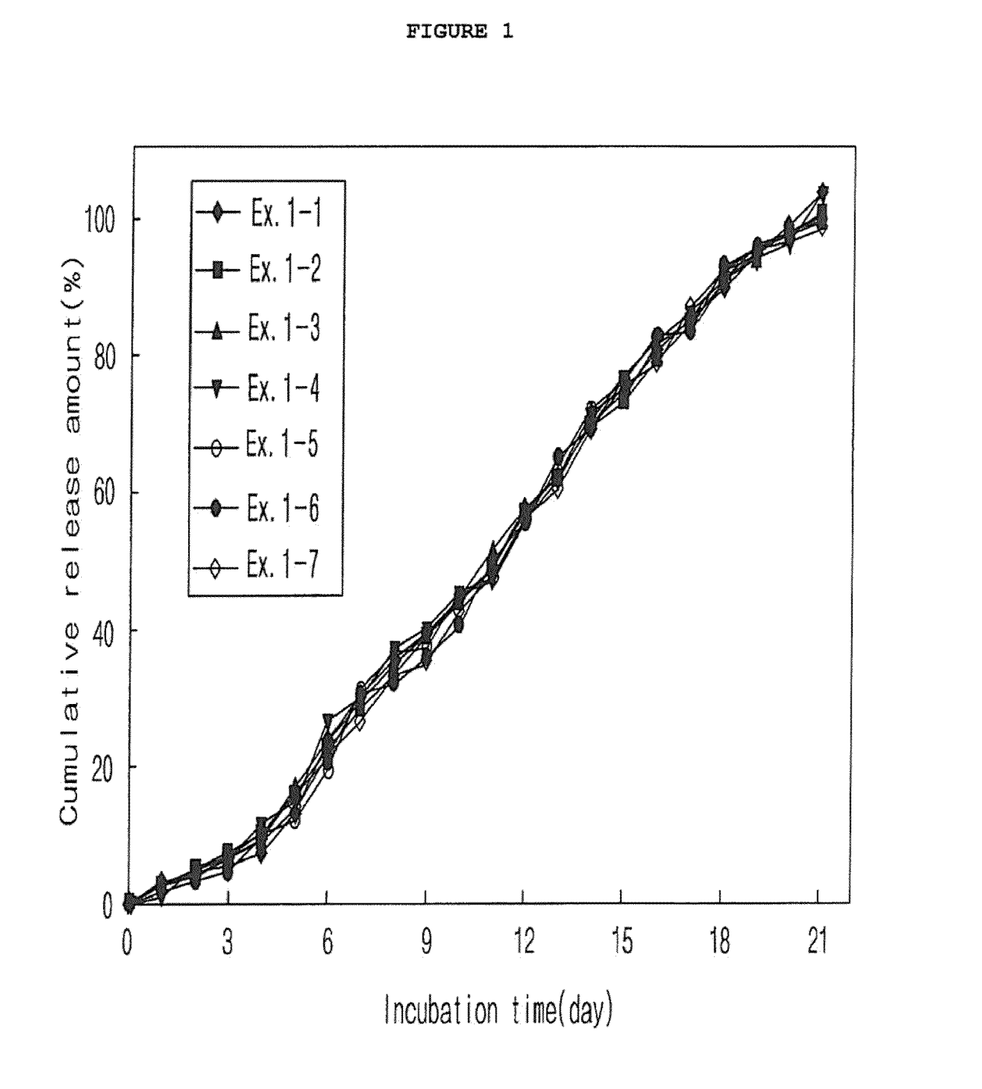
FIG. 1 is a graph showing the in vitro release pattern of the microspheres prepared through a drug dispersion process in Example 1 in accordance with the present invention.
Figure 2:
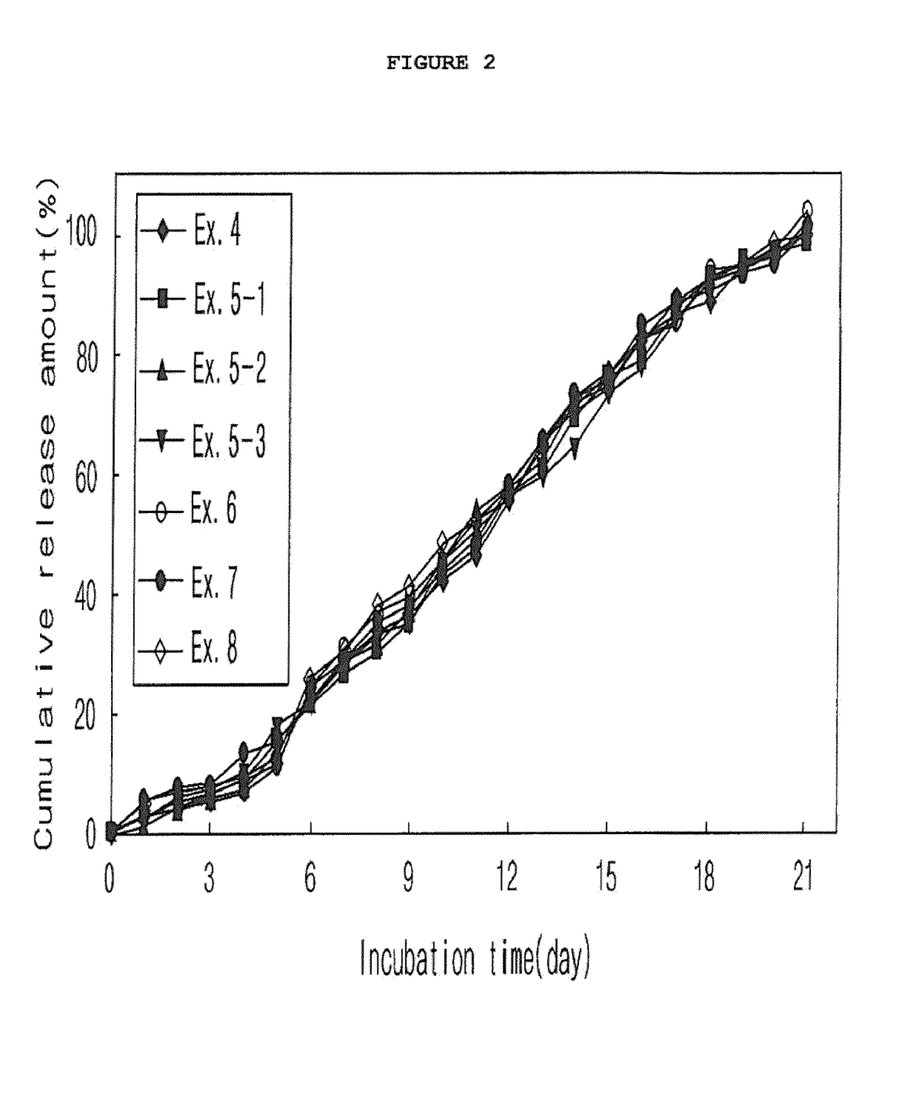
FIG. 2 is a graph showing the in vitro release patterns of the microspheres prepared in Examples 4 to 8 in accordance with the present invention.

FIGS. 1 and 2 show the amounts of exendin-4 released in vitro over time from the microspheres prepared through an exendin dispersion process according to the present invention in Examples 1 and 4-8 while FIG. 3 shows the amounts of exendin-4 released in vitro over time from the microspheres prepared in Comparative Examples 1 and 2 when the exendin dispersion process was excluded.

As is apparent from the plots of FIGS. 1 and 2, the microspheres prepared through the exendin dispersion process according to the present invention show neither initial burst release (exendin-4 released 3% during the first one day), nor incomplete release, with the maintenance of zero-order release over 21 days.

In contrast, as seen in FIG. 3, the microspheres prepared without an exendin dispersion process showed incomplete release, with only 83% (Comparative Example 1) and 49% (Comparative Example 2) released over 21 days.

Thus, the exendin 4 containing microspheres prepared in accordance with the present invention showed neither initial burst release nor incomplete release, but maintained zero-order release of exendin-4 over three weeks and therefore can be effectively used as agents for the sustained release of exendin-4.

Experimental Example 4

Pharmacokinetic Evaluation of Microspheres

In the following conditions, the microspheres prepared in Examples and Comparative Examples were evaluated for exendin-4 release in vivo and pharmacokinetic properties.

Figure 4:
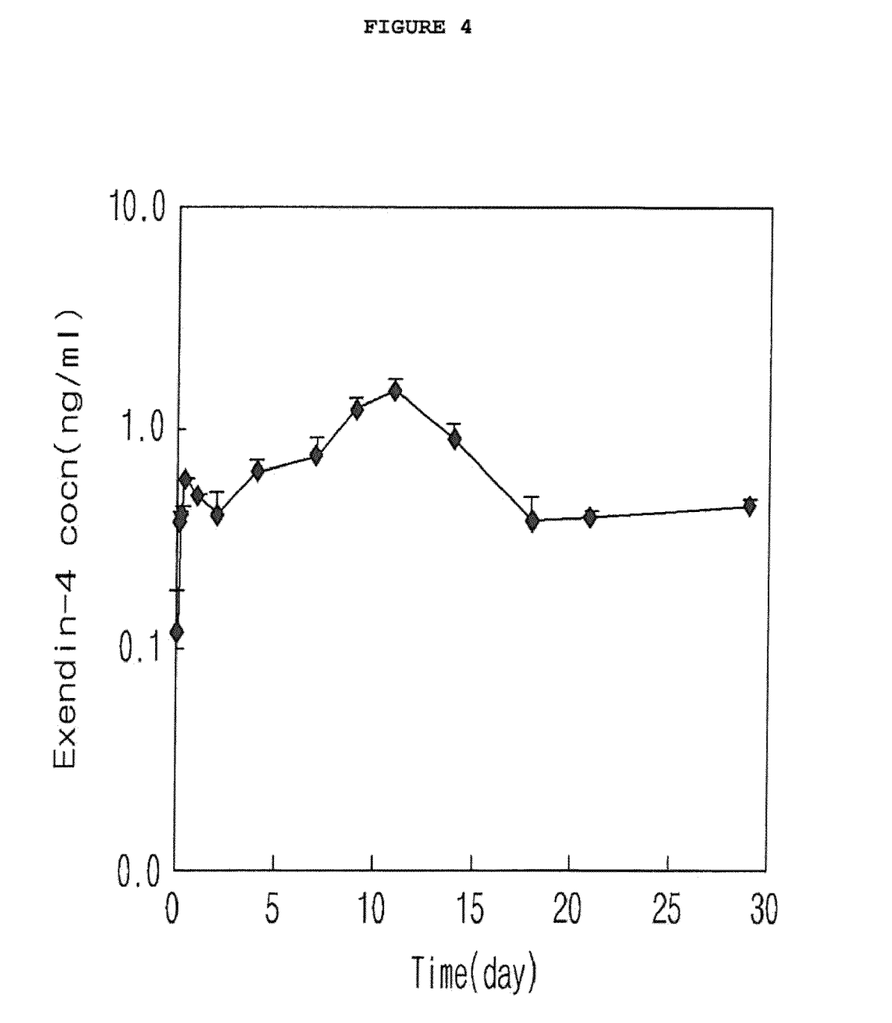
FIG. 4 shows the in vivo release pattern of the microspheres prepared in Example 1-1.

A predetermined amount of the microspheres prepared in Examples 1 and 4-8 and Comparative Examples 1 and 2 (corresponding to 140 μg of exendin-4) was suspended in an aqueous solution containing 1.5% CMC, 0.5% Tween20 and 0.9% NaCl, followed by the subcutaneous injection of the suspension at a dosage of 0.2 ml into each of five Sprague-Dawley rats. Thereafter, blood was sampled from the rats at predetermined time intervals and quantitatively analyzed for exendin-4 level using ELISA to determine the release of exendin-4 from the microspheres. FIG. 4 shows the in vivo release pattern of exendin-4 from the microspheres prepared in Example 1-1.

As is apparent from the release pattern of FIG. 4, the microspheres prepared according to the present invention show neither initial burst release nor incomplete release, but maintain zero-order release over 20 days in the experimental animals, as in the in vitro experiment.

Also, the pharmacokinetic parameters, maximum blood concentration ($C_{max}$) and $AUC_{0-14d}$, were calculated from the measurements of the exendin-4 release using a WinNonlin program, and are summarized in Table 7, below.

TABLE 7

| Examples | $C_{max}$ (ng/ml) | $AUC_{0-14d}$ (day * ng/ml/mg/kg) |
| --- | --- | --- |
| 1-1 | 1.92 ± 0.30 | 11.85 ± 0.30 |
| 1-2 | 2.78 ± 0.69 | 9.29 ± 0.57 |
| 1-3 | 1.33 ± 0.20 | 9.24 ± 0.76 |
| 1-4 | 1.18 ± 0.12 | 9.63 ± 1.08 |
| 1-5 | 1.04 ± 0.13 | 8.98 ± 0.62 |
| 1-6 | 2.26 ± 0.37 | 9.92 ± 0.81 |
| 1-7 | 4.02 ± 0.15 | 9.31 ± 0.67 |
| 4 | 1.91 ± 0.11 | 12.05 ± 0.78 |
| 5-1 | 3.13 ± 0.31 | 9.74 ± 1.08 |
| 5-2 | 1.31 ± 0.11 | 12.01 ± 0.11 |
| 5-3 | 1.29 ± 0.10 | 11.07 ± 0.91 |
| 6 | 2.05 ± 0.33 | 10.84 ± 0.78 |
| 7 | 1.67 ± 0.27 | 8.31 ± 0.27 |
| 8 | 3.28 ± 0.42 | 9.40 ± 0.58 |
| C.1 | 0.94 ± 0.17 | 5.34 ± 0.61 |
| C.2 | 0.85 ± 0.24 | 5.07 ± 0.20 |

As shown in Table 7, all of the microspheres of Examples 1-1 to 1-7, 4, 5-1 to 5-3, and 6 to 8 were calculated to be higher in $C_{max}$ and AUC values than those of Comparative Examples 1 and 2, indicating that the microspheres prepared according to the present invention are agents for the excellent controlled release of exendin-4.

On the basis of the data of FIG. 4 and Table 7, consequently, the present invention provides biodegradable polymeric microspheres which are not only excellent in encapsulation efficiency, but also can steadily release exendin-4 for 2 to 4 weeks to completion without a lag phase.

Experimental Example 5

Assay for Stability of Exendin-4 in Microsphere 10 mg of the exendin-4 containing microspheres prepared in Example 1-1 was placed in a polystyrene vessel and sufficiently dissolved in 1 ml of DMSO. The resulting solution was diluted fivefold with ammonium bicarbonate, followed by conducting reverse phase high performance liquid chromatography (RP-HPLC) to observe peaks and the retention time of exendin-4. The results are shown in FIG. 5.

Figure 5:
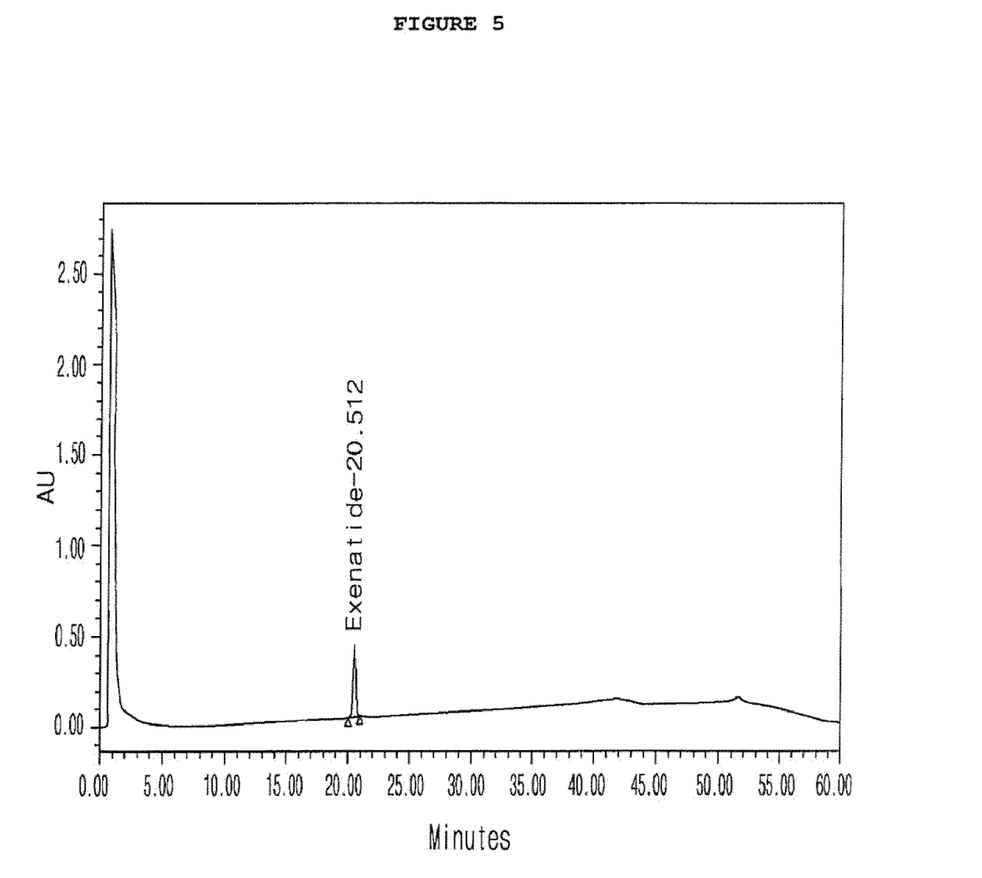
FIG. 5 is a chromatogram of the exendin-4 obtained from the microspheres prepared in Example 1-1, analyzed by reverse phase-high performance liquid chromatography (RP-HPLC).

FIG. 5 is a chromatogram of exendin-4 obtained from the microspheres prepared in Example 1-1. As seen in this chromatogram, a single peak was observed and the retention time was the same as that of the control.

The invention claimed is:
1. A method for preparing a biodegradable polymer microsphere containing a glucose-regulating peptide, comprising:
  (a) an organic solvent to a polymer to yield a polymer solution;
  (b) dispersing a glucose-regulating peptide in the polymer solution of step (a) to yield a drug dispersion;
  (c) mixing an alcohol or a mixture of an alcohol and an organic acid with the drug dispersion to yield a drug-dispersed solution; and
  (d) producing a microsphere from the drug-dispersed solution of (c),
  wherein the alcohol of step (c) is used at a ratio of 1:1~1:6 (v/v) of the alcohol: the polymer solution of step (a).
2. The method according to claim 1, wherein the organic solvent is selected form the group consisting of methylene chloride, ethylacetate and chloroform.
3. The method according to claim 1, wherein the glucose-regulating peptide is selected from the group consisting of synthetic exendin-3, exendin-4, and homologs or agonists thereof.
4. The method according to claim 1, wherein the alcohol of step (c) is methyl alcohol.
5. The method according to claim 1, further comprising an additive to the drug-dispersed solution of step (a).
6. The method according to claim 5, wherein the additive is selected from the group consisting of polyethylene glycol, oleoyl macrogolglycerides, linole macrogolglycerides or lauroyl macrogolglycerides, caprylocaproyl macrogolglycerides, medium chain triglyceride, lecithin, N-methyl pyrrolidone, polyvinyl pyrrolidone, hydropropyl methylcellulose, polysorbate, sorbitan esters, polyethoxylated castor oil, poloxamer, polyoxyethylene, and hexa(2-hydroxy-1,3-propylene glycol) diricinoleate.
7. The method according to claim 5, wherein the additive is used in an amount of 0.01 to 15% (w/v) of the volume of the solution.
8. The method according to claim 1, wherein step (d) comprises:
  dispersing the drug-dispersed solution of step 2 in an aqueous solution containing an emulsifier,
  forming the microsphere using a stirrer or a homogenizer, and
  drying the microsphere in a freeze-drying or vacuum-drying manner.
9. The method according to claim 8, wherein the emulsifier is selected from the group consisting of polyethylene glycol p-(1,1,3,3, -tetramethylbutyl)-phenyl ether, polyoxyethylene, polyvinyl pyrrolidone and polyvinyl alcohol.

10. The method according to claim 8, wherein the emulsifier is saturated in an organic solvent selected from the group consisting of methylene chloride, ethyl acetate and chloroform.

11. The method according to claim 1, wherein step (d) is carried out by spraying the drug-dispersed solution of step (c) using a spray-drier.

12. The method according to claim 11, wherein the spray drier is set at a temperature of 115~125° C. for an influx thereof and at a temperature of 80~90° C. for an efflux thereof.

13. The method according to claim 11, wherein the spray-drying is followed by additional freeze-drying or vacuum-drying.

14. The method according to claim 1, wherein the biodegradable polymer is selected from the group consisting of poly-L-lactic acid, poly-D-lactic acid-co-glycolic acid, poly-L-lactic acid-co-glycolic acid and poly-D,L-lactic acid-co-glycolic acid.

15. The method according to claim 1, wherein the alcohol is selected from the group consisting of methyl alcohol, ethyl alcohol, isopropyl alcohol and butyl alcohol.

16. The method according to claim 1, wherein the organic acid is selected from the group consisting of oxalic acid, oxaloacetic acid, fumaric acid, malic acid, succinic acid, acetic acid, butyric acid, palmitic acid, tartaric acid, ascorbic acid, uric acid, sulfonic acid, sulfinic acid, formic acid, citric acid, isocitric acid, alpha-ketoglutaric acid, succinic acid and nucleic acids, with preference for acetic acid, formic acid and a combination thereof.

* * * * *